(12) United States Patent
Hayoz et al.

(10) Patent No.: US 8,527,023 B2
(45) Date of Patent: Sep. 3, 2013

(54) DEVICE AND METHOD FOR TRANSCUTANEOUS DETERMINATION OF BLOOD GASES

(75) Inventors: Josef Hayoz, Fullinsdorf (CH); Rolf Wagner, Ettingen (CH)

(73) Assignee: Sentec AG, Therwil (CH)

( * ) Notice: Subject to any disclaimer, the term of this patent is extended or adjusted under 35 U.S.C. 154(b) by 719 days.

(21) Appl. No.: 12/597,813

(22) PCT Filed: Apr. 28, 2008

(86) PCT No.: PCT/EP2008/055189
§ 371 (c)(1),
(2), (4) Date: Oct. 27, 2009

(87) PCT Pub. No.: WO2008/132205
PCT Pub. Date: Nov. 6, 2008

(65) Prior Publication Data
US 2010/0130842 A1 May 27, 2010

(30) Foreign Application Priority Data
Apr. 27, 2007 (EP) .................................. 07107130

(51) Int. Cl.
*A61B 5/00* (2006.01)
(52) U.S. Cl.
USPC ............................ 600/326; 600/323; 604/505
(58) Field of Classification Search
USPC .......................... 600/326, 335, 323; 604/505
See application file for complete search history.

(56) References Cited

U.S. PATENT DOCUMENTS

| 4,259,963 | A | * | 4/1981 | Huch | 600/359 |
| 4,324,256 | A | | 4/1982 | Vesterager | |
| 4,488,557 | A | * | 12/1984 | Engel | 600/357 |

(Continued)

FOREIGN PATENT DOCUMENTS

| GB | 1461345 A | 1/1977 |
| GB | 2033575 | 5/1980 |
| WO | WO80/02795 | 12/1980 |
| WO | WO 02/41770 | 5/2005 |

OTHER PUBLICATIONS

Enkema L Jr et al, "Laser Doppler velocimetry vs heater power as indicators of skin perfusion during transcutaneous O2 monitoring", Clinical Chemistry, Mar. 1981, 391-396, vol. 27, No. 3.

(Continued)

*Primary Examiner* — Clayton E LaBalle
*Assistant Examiner* — Warren K Fenwick
(74) *Attorney, Agent, or Firm* — Pearl Cohen Zedek Latzer, LLP

(57) ABSTRACT

The device for the transcutaneous determination of blood gases including a transcutaneous sensor for the measurement of at least one of the parameters of skin carbon dioxide partial pressure (PsCO2) and skin oxygen partial pressure (PsO2) includes at least one sensor for the measurement of the tissue blood flow (F) local with respect to the transcutaneous sensor, and includes a device for the calculation of at least one of the parameters of transcutaneous carbon dioxide partial pressure (tcpCO2) and transcutaneous oxygen partial pressure (tcpO2) from the measured skin carbon dioxide partial pressure (PsCO2) or the measured skin oxygen partial pressure (PsO2), with a factor dependent on the local tissue blood flow (F) being taken into account in the calculation of at least one of the parameters of transcutaneous carbon dioxide partial pressure (tcpCO2) and transcutaneous oxygen partial pressure (tcpO2).

25 Claims, 2 Drawing Sheets

(56) References Cited

U.S. PATENT DOCUMENTS

| | | | |
|---|---|---|---|
| 4,539,994 A | | 9/1985 | Baumbach et al. |
| 4,930,506 A | * | 6/1990 | Ullrich .......................... 600/326 |
| 5,007,424 A | * | 4/1991 | Ahsbahs et al. .............. 600/354 |
| 5,088,493 A | * | 2/1992 | Giannini et al. .............. 600/323 |
| 5,425,868 A | | 6/1995 | Pedersen |
| 5,830,135 A | * | 11/1998 | Bosque et al. ................ 600/323 |
| 2002/0062070 A1 | * | 5/2002 | Tschupp et al. .............. 600/322 |
| 2005/0277818 A1 | | 12/2005 | Myers |
| 2011/0060204 A1 | * | 3/2011 | Weston .......................... 600/364 |

OTHER PUBLICATIONS

Jacobsen E. et al., Relationship Between Arterial and Heated Skin Surface Carbon Dioxide Tension in Adults, ACTA Anaesthesiologica Scandinavica, XX, XX, vol. 29, No. 2., Jan. 1, 1985, pp. 198-202.

Wimberley, Peter D et al., "Transcutaneous Carbon Dioxide and Oxygen Tension Measured at Different Temperatures in Healthy Adults" Clin. Chem, vol. 31, No. 10, 1985.

Swain, I. D. et al., "Methods of measuring skin blood flow" Phys. Med. Biol., vol. 34, No. 2, 1989.

General Electric publication, "Critical Care Monitoring, Clinical Reference and Troubleshooting Guide" General Electric publication, Revision A, Jan. 31, 2005.

Parker, D. et al., "A Transcutaneous PO2 Electrode Incorporating a Termal Clearance Local Blood Flow Sensor" Acta anaesth. scand., vol. Sup.68, 1978.

Beran, Anthony V. et al., "Cutaneous blood flow and its relationship to transcutaneous O2/CO2 measurements" Critical Care Medicine, vol. 9, No. 10, 1981.

Baumbach, Per, "Understanding Transcutaneous pO2 and pCO2 measurements" Radiometer publication TC100, 1986, ISBN: 87-88138-11-9.

Baumbach, Per, ""TC100: Understanding Transcutaneous pO2 and pCO2 measurements""Radiometer publications, 2008, ISBN: 87-88138-11-9.

Steinacker, J. M. et al., "Dependence of transcutaneous O2 partial pressure on cutaneous blood flow" J Appl Physiol, vol. 64, 1988.

Palmisano, Barbara W. et al., "Transcutaneous PCO2 and PO2: A Multicenter Study of Accuracy" J Clin Manit, No. 6, 1990.

Thunstrom, Avghi M. et al., "A Two Temperature, Two PO2 Method of Estimating the Determinants of tcPO2" Birth Defects: Original Article Series, vol. XV, No. 4, 1979.

European Notice of Opposition for European Patent Application No. EP2144555, dated Feb. 27, 2013.

* cited by examiner

DEVICE AND METHOD FOR TRANSCUTANEOUS DETERMINATION OF BLOOD GASES

CROSS-REFERENCE TO RELATED APPLICATIONS

This application is a national phase application of International Application PCT/EP2008/055189 filed on Apr. 28, 2008, which in turn claims priority from European application 07107130.2, filed on Apr. 27, 2007, each of which are incorporated by reference herein in their entirety.

FIELD OF THE INVENTION

The invention relates to a device for the transcutaneous determination of blood gases in accordance with the preamble of claim 1. The invention further relates to a method for the transcutaneous determination of blood gases in accordance with the preamble of claim 12.

PRIOR ART

The knowledge of the concentration of blood gases in the arterial blood, or of the arterial carbon dioxide partial pressure (PaCO2) and of the arterial oxygen partial pressure (PaO2), are of importance for the determination and monitoring of the respiratory status of a patient. Since the respiratory status of a patient can change very fast and since in particular hypoxias or hypercapnias can disadvantageously impair the state of the patient, a continuous and, ideally, non-invasive monitoring of the blood gases is necessary in many cases.

The gases carbon dioxide (CO2) and oxygen (O2) have the property that they diffuse through the tissue of the body and in particular through the skin. It is therefore possible using a so-called transcutaneous sensor—a suitable sensor lying on the skin surface—to measure the skin carbon dioxide partial pressure (PaCO2) or the skin oxygen partial pressure (PaO2) in the region of the sensor in a non-invasive and continuous manner and to determine from this by means of suitable processes a so-called transcutaneous carbon dioxide partial pressure (tcpCO2) or a transcutaneous oxygen partial pressure (tcpO2). The index "s" used for PsCO2 and PsO2 has the meaning of skin.

The transcutaneous carbon dioxide partial pressure (tcpCO2) or the transcutaneous oxygen partial pressure (tcpO2) should ideally be determined such that it corresponds to the arterial carbon dioxide partial pressure (PaCO2) or to the arterial oxygen partial pressure (PaO2). Substantial differences have previously often occurred between these values, which unfortunately means that the transcutaneous determination of blood gases is often incorrect.

Document WO 02/41770 discloses such devices and methods, for example for the determination of the transcutaneous carbon dioxide partial pressure (tcpCO2) in accordance with Stow-Severinghaus or of the transcutaneous oxygen partial pressure (tcpO2) in accordance with Clark. The transcutaneous sensor lying on the skin used in this respect also has, in addition to the CO2 sensors or O2 sensors used for the measurement of the skin carbon dioxide partial pressure (PsCO2) and of the skin oxygen partial pressure (PsO2) respectively, a heating element which typically heats the skin in the region of the sensor to a constant temperature (Ts) which is higher than the usual body surface temperature.

The following equation (1) proposed by Severinghaus is used to determine the transcutaneous carbon dioxide partial pressure for a given reference temperature Tr from the skin carbon dioxide partial pressure (PsCO2(Ts)) measured at the skin temperature Ts:

$$tcpCO2(Tr) = \frac{PsCO2(Ts)}{10^{(Ts-Tr) \times A}} - Ms \tag{1}$$

where the parameters used have the following meaning:
Ts: Temperature of the skin in the region of the sensor
Tr: Reference temperature, typically 37° C.
PsCO2(Ts): The skin carbon dioxide partial pressure present at the temperature Ts in the region of the sensor
Ms: The metabolic offset
A: Anaerobic temperature factor The first term of the equation (1) corrects the value of PsCO2(Ts) measured at a skin temperature of Ts to the reference temperature Tr, while using the anaerobic temperature factor (A). The constant Ms called the metabolic offset takes account of the remaining distance between the skin carbon dioxide partial pressure and the arterial carbon dioxide partial pressure.

The aforesaid equation (1) is also known from the literature in the following slightly modified form:

$$tcpCO2(Tr) = \frac{PsCO2(Ts) - Ms}{10^{(Ts-Tr) \times A}}$$

The following equation (2) proposed by Clark is used to determine the transcutaneous oxygen partial pressure for a given reference temperature Tr from the skin oxygen partial pressure (PsO2(Ts)) measured at the skin temperature Ts:

$$tcpO2(Tr) = Corr * PsO2(Ts) \tag{2}$$

where the parameter used has the following meaning:
Corr: Correction factor

The fact is disadvantageous in known sensors or in the correction procedure shown in the equation (1) that substantial deviations can occur between the transcutaneous carbon dioxide partial pressure (tcpCO2(Tr)) determined by means of equation (1) and the carbon dioxide partial pressure (PaCO2(Tr)) effectively present in the arterial blood at the reference temperature Tr. The same applies to the transcutaneous oxygen partial pressure (tcpO2(Tr)) which is determined by means of equation (2) and which can likewise have substantial deviations to the oxygen partial pressure (PaO2(Tr)) effectively present in the arterial blood.

SUMMARY

It is therefore the object of the present invention to propose a device and a method to improve the coincidence between the transcutaneous carbon dioxide partial pressure (tcpCO2(Tr)) or the transcutaneous oxygen partial pressure (tcpO2(Tr)) and the arterial carbon dioxide partial pressure (PaCO2(Tr)) or the arterial oxygen partial pressure (PaO2(Tr)).

This object is satisfied using a device having the features of claim 1. Dependent claims 2 to 11 relate to further preferred embodiments of the device. The object is further satisfied using a method having the features of claim 12. Dependent claims 13 to 21 relate to further preferred method steps.

The object is in particular satisfied by a device for the measurement of at least one of the parameters skin carbon dioxide partial pressure (PsCO2) and skin oxygen partial pressure (PsO2), by at least one sensor for the measurement of the tissue blood flow (F) local with respect to the transcutaneous CO2 sensor and/or O2 sensor, and including a device for the calculation of at least one of the parameters of transcutaneous carbon dioxide partial pressure (tcpCO2) and transcutaneous oxygen partial pressure (tcpO2) from the measured skin carbon dioxide partial pressure (PsCO2) or the measured skin oxygen partial pressure (PsO2), with a factor dependent on the local tissue blood flow (F) being taken into account in the calculation of at least one of the parameters of transcutaneous carbon dioxide partial pressure (tcpCO2) and transcutaneous oxygen partial pressure (tcpO2)

The object is further in particular satisfied by a method for transcutaneous blood gas monitoring, wherein at least one of the parameters of skin carbon dioxide partial pressure (PsCO2) and skin oxygen partial pressure (PsO2) is detected, and wherein a local tissue blood flow is detected, and wherein at least one of the parameters of transcutaneous carbon dioxide partial pressure (tcpCO2) and transcutaneous oxygen partial pressure (tcpO2) is calculated from the measured skin carbon dioxide partial pressure (PsCO2) or the measured skin oxygen partial pressure (PsO2), wherein the local tissue blood flow (F) is taken into account in the calculation of at least one of the parameters of transcutaneous carbon dioxide partial pressure (tcpCO2) and transcutaneous oxygen partial pressure (tcpO2).

Comparative studies have in particular shown that fluctuations in the local tissue blood flow and in particular a small local tissue blood flow result in an increased deviation between the determined transcutaneous carbon dioxide partial pressure (tcpCO2) and the effective arterial carbon dioxide concentration (PaCO2). The same applies to the determined transcutaneous oxygen partial pressure (tcpO2) and the effective arterial oxygen concentration (PaO2). To reliably determine the effective arterial carbon dioxide concentration (PaCO2) from the measured skin carbon dioxide partial pressure (PsCO2), it is therefore necessary in accordance with the invention to use a blood flow correction factor F in the calculation of the transcutaneous carbon dioxide partial pressure (tcpCO2). The value F is in this respect preferably to be measured close to the transcutaneous sensor, preferably beneath the transcutaneous sensor, but at least preferably in an area of no more than 1 to 2 cm remote from the contact surface of the transcutaneous sensor. To reliably determine the effective arterial oxygen concentration (PaO2) from the measured skin oxygen partial pressure (PsO2), it can therefore be advantageous to use a blood flow correction factor F in the calculation of the transcutaneous oxygen partial pressure (tcpO2).

Starting from the skin carbon dioxide partial pressure (PsCO2(Ts)) measured at the skin temperature Ts, the transcutaneous carbon dioxide partial pressure can be calculated for a given reference temperature Tr as follows as a function of the value F (equation 1"):

$$tcpCO2(Tr, F) = \frac{PsCO2(Ts)}{10^{(Ts-Tr)\times A}} - Ms(Ts, F) \quad (1'')$$

Ts: Temperature of the skin in the region of the sensor
Tr: Reference temperature, typically 37° C.
PsCO2(Ts): The skin carbon dioxide partial pressure present at the temperature Ts in the region of the sensor
Ms(Ts, F): The metabolic offset present at the temperature Ts in the region of the sensor as a function of the value F. In a simple correction, Ms is only corrected in dependence on F.

In a more demanding version, the metabolic offset is also corrected in dependence on Ts. The simplified equation 1" thus only corrects Ms(F).
A: Anaerobic temperature factor A further relationship, which is very similar to equation 1", results if Ms is also divided by the denominator so that a separate correction of Ms with respect to the temperature Ts is not necessary since this is done via the denominator:

$$tcpCO2(Tr, F) = \frac{PsCO2(Ts) - Ms(F)}{10^{(Ts-Tr)\times A}}$$

Starting from the skin oxygen partial pressure (PsO2 (Ts)) measured at the skin temperature Ts, the transcutaneous oxygen partial pressure can be calculated for a given reference temperature Tr as follows as a function of the value F (equation 2"):

$$tcpO2(Tr,F) = Corr(Tr,Ts,F)*PsO2(Ts) \quad (2'')$$

where the parameter used has the following meaning:
Corr(Tr, Ts, F): Correction factor dependent on the reference temperature Tr, on the skin temperature Ts present in the region of the sensor and on the value F. In a simplified version, the correction factor is only corrected as a function of the value F so that only the factor Corr (F) is taken into account in a simplified equation 2".

A substantial advantage of the device in accordance with the invention or of the method in accordance with the invention can be seen in the fact that the influence of the blood flow is reduced or eliminated which resulted in a deviation between the transcutaneous carbon dioxide partial pressure (tcpCO2(Tr)) or the transcutaneous oxygen partial pressure (tcpO2(Tr)) and the arterial carbon dioxide partial pressure (PaCO2(Tr)) or the arterial oxygen partial pressure (PaO2 (Tr)). The value F preferably designates the blood flow, with the value F also being able to be a different measurement parameter which can serve as a measure for the local tissue blood flow or for the local perfusion of the skin. In particular measurement parameters are of interest which take account of the local availability of gases, in particular the availability of arterial gases, the blood quantity which has flowed in or the blood quantity which has been transported off, or the pulsation. A measurable value is thus understood by the term "tissue blood flow" which in particular permits the local availability or the locally present quantity of arterial gases to be detected. Thanks to the knowledge of the tissue blood flow, it is possible to correct the measured values such that the determined value for the transcutaneous carbon dioxide partial pressure (tcpCO2(Tr)) or of the transcutaneous oxygen partial pressure (tcpO2(Tr)) no longer depends or only slightly depends on the tissue blood flow. In other words, the device in accordance with the invention or the method in accordance with the invention permits a correction dependent on the perfusion or on the blood flow in order thereby to reduce or eliminate the influence on the determined values effected by the perfusion or the tissue blood flow. A plurality of possibilities are known to measure the perfusion or blood flow, a value equivalent to or similar to the perfusion or blood flow or the value F of the tissue blood flow. The pulse volume modulation, also called the "total pulse modulation TPM", could thus be measured for example, in order to calculate the value F from it. The flow F, that is, for example, the volume per second, can be measured in very different manners. It is important that the flow F is measured locally, that is where possible in the proximity of or beneath the transcutaneous sensor. The flow F can, for example, be measured beneath the transcutaneous sensor using the methods named by way of example in the following:

1. Doppler scan: The flow or the tissue blood flow F of the blood can be determined utilizing the Doppler effect, for example by an optical or acoustic measurement.
2. (Photo)plethysmographic measurement system: The flow or the tissue blood flow F of the blood can be measured using a (photo)plethysmographic measurement system, in particular using a pulse spectrographic measurement system. To determine a measure for the tissue blood flow F, the AC voltage portion and/or the DC voltage portion of the measured light signals can be used in a photoplethysmographic measurement.
3. Spectroscopic measurement: The tissue blood flow F can also be measured optically by measurement of the spectrum, in particular in the near infrared (NIR), for example using a device and a method as are disclosed in the document US 2005/0277818 A1.
4. Heat energy: Measurement of the heat energy which is required to maintain a device lying on the skin at a constant temperature, with this temperature being higher than the skin temperature. It applies that with a larger flow F a higher heat energy is required to keep the temperature constant so that the flow F can be estimated via the required heat energy.

Depending on the selected measurement method, the value F can also be measured for difficult, but clinically important situations such as arterial hypotension, hypovolemia after blood losses of the patient or vasoconstriction of the peripheral small arteries. These three described states are clinically frequent, in particular in intra-operative and post-operative applications. In these states, blood can be found at the application point, with this, however, no longer being sufficiently replenished by a blood import. Such a situation can also be detected using the value F. Such a state can, for example, be detected using a photoplethysmographic measurement system which derives an AC voltage signal and a DC voltage signal from a detected light signal. It must be taken into account that the device in accordance with the invention or the method in accordance with the invention cannot determine the local perfusion absolutely, but only approximately. This determined local perfusion, however, allows the measurement quality of transcutaneously determined blood gas values to be substantially improved. The value F could include a further correction factor, namely local skin properties, because the correction can also depend on further local skin properties in addition to the blood flow. These local skin properties can, for example, be measured via the DC voltage signal of the photoplethysmographic measurement system since the total absorption capability of the tissue can be measured with this measurement signal, not only the portion of the flowing hemoglobin. This measurement signal is therefore preferably a measure for the total optical density and therefore permits a conclusion on the histoanatomy of the measurement site. A value F determined or corrected in this manner permits the measurement quality of transcutaneously determined blood gas values to be substantially improved.

BRIEF DESCRIPTION OF THE DRAWINGS

The drawings used to explain the embodiments show.

Generally, the same parts are provided with the same reference numerals in the drawings.

DETAILED DESCRIPTION

Figure 1:
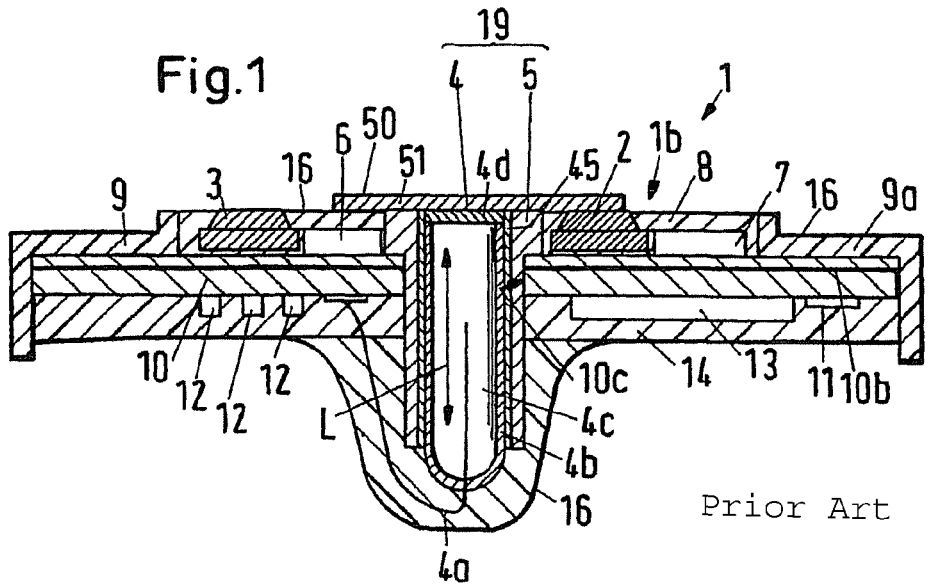
FIG. 1 a longitudinal section through a known transcutaneous sensor.
Figure 2:
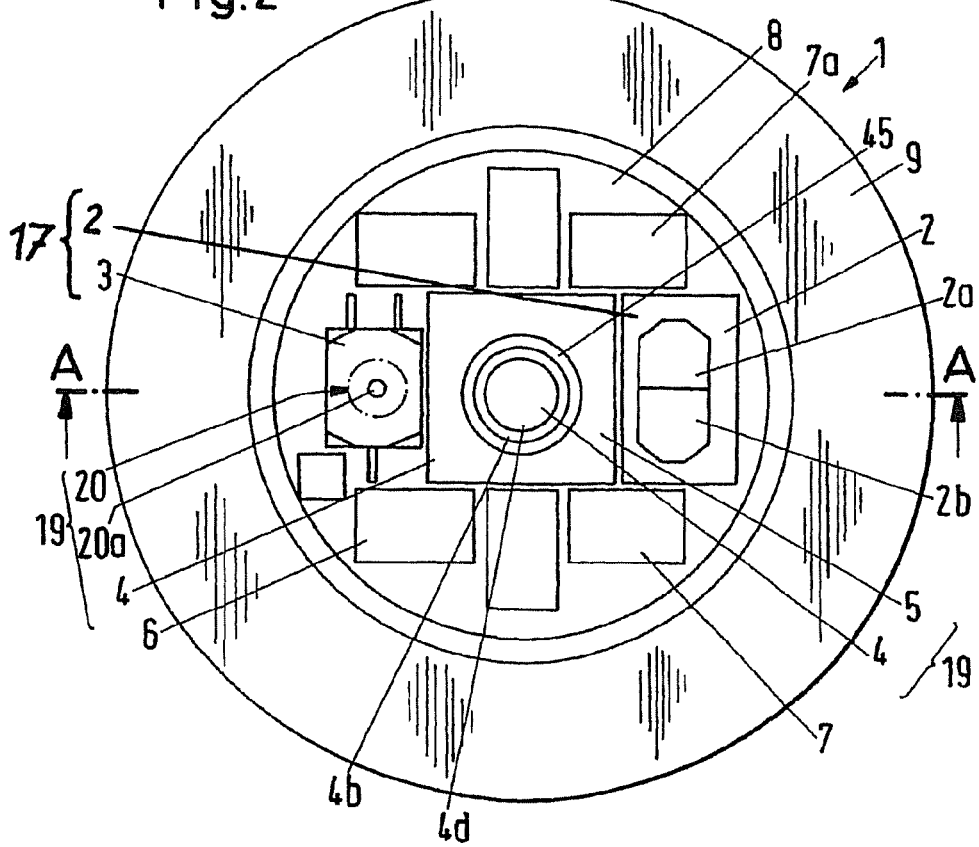
FIG. 2 a plan view of the transcutaneous sensor shown in FIG. 1.

The sensor 1 shown in FIGS. 1 and 2 is known from document WO 02/41770 The sensor 1 shown allows a combined measurement of the arterial oxygen saturation (SpO2) and of the transcutaneous CO2 partial pressure (tcpCO2). For the measurement of the oxygen saturation, the sensor 1 has a pulse oximetric measurement system 17 which includes, among other things, a two-color light emitting diode 2 (LED) as well as a photodetector 3. The two-color light emitting diode 2 includes two light emitting diodes 2a, 2b disposed closely next to one another and arranged in a common housing, with the one light emitting diode 2a having a wavelength of approximately 660 μm (red) and the other light emitting diode 2b having a wavelength of approximately 890 μm (infrared). The sensor 1 has a surface 1b over which, in the embodiment shown, a membrane 50 is arranged and therebetween a thin layer of electrolyte 51. This membrane 50 is placed on the skin at a point of the human body which has a good blood flow, for example at a finger, at the forehead or at the earlobe. The light transmitted by the two light emitting diodes 2a, 2b radiates through the electrolyte 51 located above the light emitting diodes 2a, 2b and through the membrane 50 and is conducted into the body part, not shown, with a good blood flow and is scattered there and partly absorbed. The light reflected by the body part is measured using the photodetector 3. The signal measured by the photodetector 3 is supplied to a digital sensor signal processor 13.

The sensor 1 shown moreover includes an electrochemical measuring device 19 for the measurement of the transcutaneous carbon dioxide partial pressure (tcpCO2 measurement), with this measuring device 19 including a micro-pH electrode 4 as well as an Ag/AgCl reference electrode 5. The transcutaneous carbon dioxide partial pressure is measured potentiometrically in that the pH of the thin layer of the electrolyte solution 51 is measured which is in communication with the skin via the hydrophobic membrane 50 which has good gas permeability. A change in the pCO2 value at the skin surface effects a pH change of the electrolyte solution which behaves proportionally to the logarithm of the pCO2 change. The pH is measured in that the potential is measured between the miniature pH electrode 4 and the Ag/AgCl reference electrode 5. The micro-pH electrode 4 is conductively connected via the electrical inner deflector 4a to the digital sensor signal processor 13.

The sensor 1 shown moreover includes a heating system 18 including a heating device 6 configured as an electrical resistor and a temperature sensor 7 for the temperature regulation. The heating system 18 is advantageously used in combination with the electrochemical measuring device 19 to heat via the sensor surface 1b the skin located thereunder. For the transcutaneous measurement of the carbon dioxide partial pressure pCO2 or of the oxygen partial pressure pO2, the sensor surface 1b is, for example, heated to a temperature of approximately 40° C. to 44° C.

The sensor 1 includes a multilayer, rigid circuit board 10 which is equipped with electronic components 2, 3, 6, 7, 12, 13 and which has a plurality of electrical conductor tracks, not shown, to connect the electronic components, such as the light emitting diode 2, the photodetector 3, the resistor 6, the temperature sensor 7, a second temperature sensor 7a or further electronic components such as amplifiers 12, 12a in a signal conductive manner.

Figure 3:
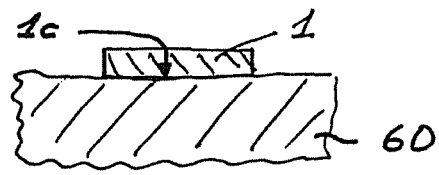
FIG. 3 a longitudinal section through a transcutaneous sensor lying on the skin.

FIG. 3 shows a longitudinal section through a sensor 1 lying on the skin 60. The sensor for the measurement of the local tissue blood flow F is preferably configured such that it measures the local tissue blood flow F beneath the contact surface of the transcutaneous sensor or beneath the contact surface 1c of the whole sensor 1. The local tissue blood flow F is preferably measured approximately in a region of up to 4 cm distance from the sensor 1 and preferably in a region from up to 2 cm distance from the contact surface 1c of the sensor 1.

The sensor 1 shown in FIG. 1 has a pulse oximetric measurement system 17 which was previously used for the measurement of the oxygen saturation. The pulse oximetric measurement system 17 can, however, also be used for the measurement of the tissue blood flow F. The pulse oximetric measurement system 17 shown in FIG. 1 is in a position to determine the tissue blood flow F by a corresponding calculation via the light which is irradiated from the two-color light emitting diode 2, reflected in the skin and measured by the photodetector 3. The local tissue blood flow F can thereby be determined beneath the contact surface 1a of the sensor 1.

The local tissue blood flow F can also be determined, for example, using a heating device in that, for example, it keeps the temperature of the sensor contact surface constant, with the power supplied to the heating device representing a measure for the tissue blood flow F.

Figure 4:
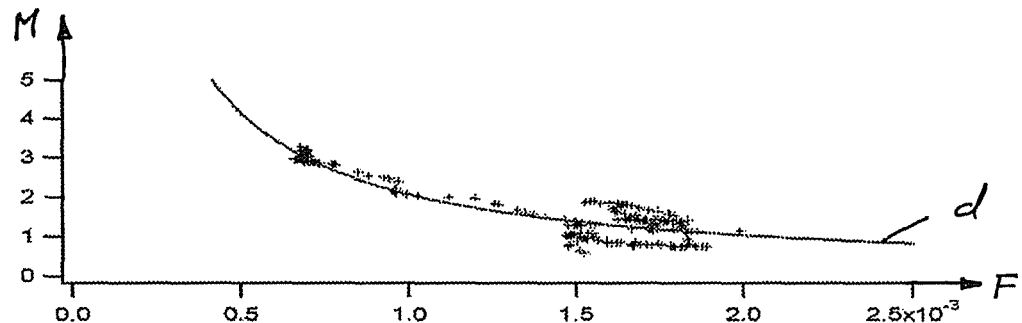
FIG. 4 a graphical representations of the correction of the metabolic offset Ms as a function of the tissue blood flow F.

FIG. 4 shows the relationship of the metabolic offset Ms as a function of the local tissue blood flow F, with F having been determined pulse oximetrically in the embodiment shown, for example using a sensor as shown in FIGS. 1 and 2. The local tissue blood flow could also be measured pulse spectroscopically using a different device. If moreover, as indicated in equation 1", the temperature Ts is taken into account, a curve group would thus result in FIG. 4 of curves substantially displaced with respect to one another in the vertical direction in particular as a function of the temperature Ts.

Figure 5:
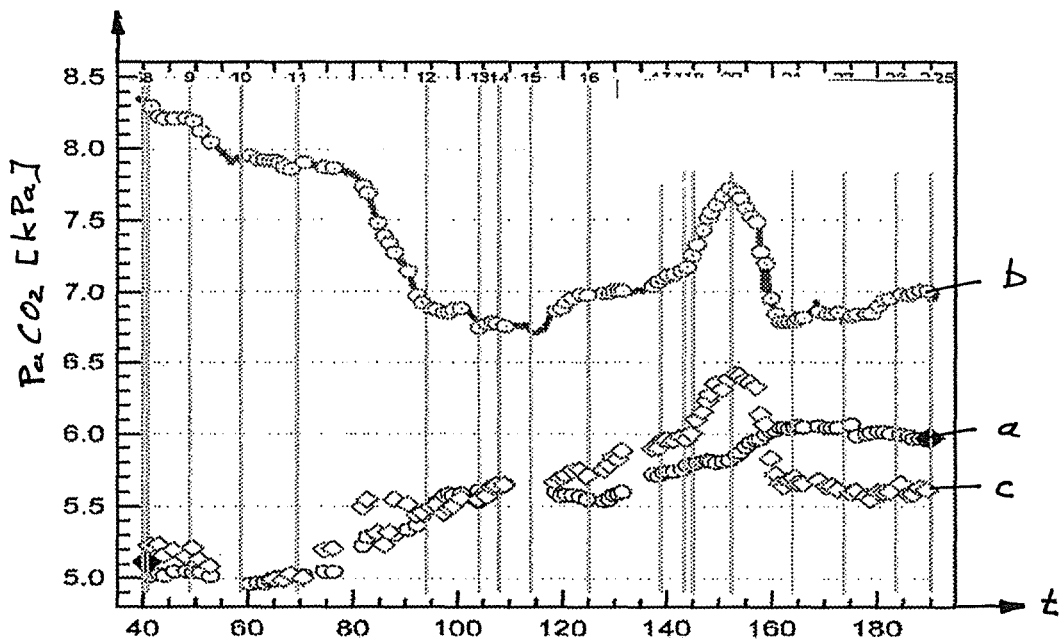
FIG. 5 a graphical representation of the time course of the arterial carbon dioxide partial pressure (curve a) determined by means of blood gas analysis as well as of the transcutaneous carbon dioxide partial pressure determined by means of equation 1 (uncorrected, curve b) or by means of equation 1" (flow-corrected, curve c). All the curves are shown for the same reference temperature (Tr=37° C.).

FIG. 5 shows different carbon dioxide partial pressure curves. The curve a shows the carbon dioxide partial pressure (PaCO2(37° C.)) effectively present in the blood and determined by means of arterial blood gas analysis for a reference temperature of 37° C. The curves b and c respectively represent the time development of the transcutaneous carbon dioxide partial pressure (tcpCO2(37° C.)) calculated—starting from the skin carbon dioxide partial pressure (PsCO2(42° C.)) measured at 42° V using the sensor 1 shown in FIGS. 1 and 2—using equation 1 or using equation 1" (without taking account of a temperature correction in the metabolic offset Ms) for a reference temperature of 37° C. In the calculation by means of equation 1" (curve c), the dependence shown in FIG. 4 of the metabolic offset Ms on the local tissue blood flow F is used. As can be seen from FIG. 5, the course of curve b differs considerably from the course of curve a, whereas the course of curve c substantially corresponds to the course of the curve a. This means that the time development of the transcutaneous carbon dioxide partial pressure (tcpCO2(37° C.) determined by means of equation 1" coincides very well with the time development of the effective carbon dioxide partial pressure (PaCO2(37° C.). The device in accordance with the invention, or the method in accordance with the invention, thus allows the course of the carbon dioxide partial pressure PaCO2 to be determined very accurately. The taking into account of the tissue blood flow F for the correction of measured values is in particular of importance when the blood flow of the skin beneath the sensor is small since then the CO2 produced by the metabolism can no longer be transported away efficiently by the blood. The method in accordance with the invention thus has the advantage that the concentration of blood gases in the arterial blood can also be measured safely and reliably in patients with circulatory disorders, low blood flow or changing blood flow. The device in accordance with the invention and the method in accordance with the invention respectively thus allow difficult patients and thus patients very demanding with respect to monitoring to be monitored safely and reliably also with respect to circulation and blood flow.

The invention claimed is:

1. A device for a transcutaneous determination of blood gases comprising:
a transcutaneous sensor for a measurement of at least one of the parameters of skin carbon dioxide partial pressure (PsC02) and skin oxygen partial pressure (Ps02), at least one sensor for a measurement of a tissue blood flow (F) local with respect to the transcutaneous sensor, and a device for the calculation of at least one of the parameters of transcutaneous carbon dioxide partial pressure (tcpC02) and transcutaneous oxygen partial pressure (tcp02) from the measured skin carbon dioxide partial pressure (PsC02) or the measured skin oxygen partial pressure (Ps02) respectively, with a factor dependent on the local tissue blood flow (F) being taken into account in a calculation of at least one of the parameters of transcutaneous carbon dioxide partial pressure (tcpC02) and transcutaneous oxygen partial pressure (tcp02),
wherein the determination of the transcutaneous carbon dioxide partial pressure (tcpC02) takes place in accordance with the equation:

$$tcpCO2(Tr, F) = \frac{PsCO2(Ts)}{10^{(Ts-Tr) \times A}} - Ms(F)$$

while taking account of the local tissue blood flow (F).

2. A device in accordance with claim 1, wherein the determination of the transcutaneous carbon dioxide partial pressure (tcpCO2) takes place in accordance with the equation:

$$tcpCO2(Tr, F) = \frac{PsCO2(Ts)}{10^{(Ts-Tr) \times A}} - Ms(Ts, F)$$

while additionally taking account of the local temperature (Ts).

3. A device in accordance with claim 1, wherein the determination of the transcutaneous oxygen partial pressure (tcpO2) takes place in accordance with the equation tcpO2(Tr,F)=Corr(F)*PsO2(Ts) while additionally taking account of the local tissue blood flow (F).

4. A device in accordance with claim 1, wherein the determination of the transcutaneous oxygen partial pressure (tcpO2) takes place in accordance with the equation tcpO2(Tr,F)=Corr(Tr,Ts,F)*PsO2(Ts) while taking account of the local temperature (Ts).

5. A device in accordance with claim 1, wherein the at least one sensor for the measurement of the local tissue blood flow (F) is arranged in the same housing as the transcutaneous sensor.

6. A device in accordance with claim 1, wherein the at least one sensor for the measurement of the local tissue blood flow (F) are configured such that they measure the local tissue blood flow (F) beneath the contact surface of the transcutaneous sensor.

7. A device in accordance with claim 1, wherein the at least one sensor for the measurement of the local tissue blood flow (F) detect a region of up to 4 cm distance from the contact surface of the transcutaneous sensor.

8. A device in accordance with claim 1, wherein the at least one sensor for the measurement of the local tissue blood flow (F) are part of a (photo)plethysmographic measurement system.

9. A device in accordance with claim 8 wherein the (photo) plethysmographic measurement system is selected from the group consisting of a pulse spectroscopic and a pulse oximetric measurement system.

10. A device in accordance with claim 1, wherein the at least one sensor for the measurement of the local tissue blood flow (F) are part of a heating device which keeps the temperature of the contact surface constant, with the power supplied to the heating device being a measure for the tissue blood flow (F).

11. A device in accordance with claim 1, wherein the at least one sensor for the measurement of the local tissue blood flow (F) are configured as acoustic sensors or as light sensors and form part of a Doppler measurement system.

12. A device in accordance with claim 1, wherein the at least one sensor for the measurement of the local tissue blood flow (F) is configured as a laser sensor, and forms part of a Doppler measurement system.

13. A method for transcutaneous blood gas monitoring, comprising:
detecting at least one of the parameters of skin carbon dioxide partial pressure (PsCO2) and skin oxygen partial pressure (PsO2), and detecting a local tissue blood flow (F), and calculating at least one of the parameters of transcutaneous carbon dioxide partial pressure (tcpCO2) and transcutaneous oxygen partial pressure (tcpO2) from the measured skin carbon dioxide partial pressure (PsCO2) or the measured skin oxygen partial pressure (PsO2), wherein the local tissue blood flow (F) is taken into account in the calculation of at least one of the parameters of transcutaneous carbon dioxide partial pressure (tcpCO2) and transcutaneous oxygen partial pressure (tcpO2),
wherein the transcutaneous carbon dioxide partial pressure (tcpCO2) is calculated as a function of the tissue blood flow (F) in accordance with the equation $$tcpCO2(Tr, F) = \frac{PsCO2(Ts)}{10^{(Ts-Tr) \times A}} - Ms(F).$$

14. A method in accordance with claim 13, wherein the transcutaneous carbon dioxide partial pressure (tcpCO2) is additionally calculated as a function of the local temperature (Ts) in accordance with the equation $$tcpCO2(Tr, F) = \frac{PsCO2(Ts)}{10^{(Ts-Tr) \times A}} - Ms(Ts, F).$$

15. A method in accordance with claim 13, wherein the transcutaneous oxygen partial pressure (tcpO2) is calculated as a function of the tissue blood flow (F) in accordance with the equation tcpO2(Tr,F)=Corr(Tr,Ts,F)*PsO2(Ts).

16. A method in accordance with claim 15, wherein the transcutaneous oxygen partial pressure (tcpO2) is additionally calculated as a function of the local temperature (Ts) in accordance with the equation tcpO2(Tr,F)=Corr(Tr,Ts,F) *PsO2(Ts).

17. A method in accordance with claim 13, wherein a transcutaneous sensor has a contact surface; and the local tissue blood flow (F) is measured within the region determined by the contact surface.

18. A method in accordance with claim 13, wherein a transcutaneous sensor has a contact surface; and the local tissue blood flow (F) is measured within a region of up to 4 cm, and preferably within a region of up to 2 cm, distance from the contact surface of the transcutaneous sensor.

19. A method in accordance with claim 13, wherein the local tissue blood flow (F) is determined using a (photo) plethysmographic measurement system.

20. A method in accordance with claim 13, wherein the local tissue blood flow (F) is determined using a heating device which keeps the temperature of the contact surface constant, with the power supplied to the heating device being a measure for the tissue blood flow (F).

21. A method in accordance with claim 13, wherein the local tissue blood flow (F) is determined using acoustic sensors or light sensors which are part of a Doppler scan system.

22. A method in accordance with claim 13, wherein the local tissue blood flow (F) is determined using a pulse spectroscopic or a pulse oximetric measurement system.

23. A method in accordance with claim 13, wherein the local tissue blood flow (F) is determined using laser sensors which are part of a Doppler scan system.

24. A method comprising using a sensor for a transcutaneous determination of blood gases, the sensor comprising a transcutaneous sensor for a measurement of a skin carbon dioxide partial pressure (PsCO2) and comprising sensor for a pulse spectroscopic or pulse oximetric measurement of the arterial oxygen saturation (SpO2), the method comprising determining a local tissue blood flow (F) using the sensor for the pulse spectroscopic or pulse oximetric measurement mid calculating the transcutaneous carbon dioxide partial pressure (tcpCO2) from the measured skin carbon dioxide partial pressure (PsCO2) taking into account the local tissue blood flow (F) in accordance with the equation:

$$tcpCO2(Tr, F) = \frac{PsCO2(Ts)}{10^{(Ts-Tr) \times A}} - Ms(F).$$

25. A method comprising using a sensor for a transcutaneous determination of blood gases, the sensor comprising a transcutaneous sensor for a measurement of the skin carbon dioxide partial pressure (PsCO2), the sensor comprising a sensor for a pulse spectroscopic or pulse oximetric measurement of an arterial oxygen saturation (SpO2) and comprising a heating device, the method comprising calculating local tissue blood flow (F) wherein at least the pulse spectroscopic or pulse oximetric measurement or at least the heating device is taken into account for a determination of the local tissue blood flow (F) and comprising calculating transcutaneous carbon dioxide partial pressure (tcpC02) from the measured skin carbon dioxide partial pressure (PsC02) taking into account the local tissue blood flow (F), wherein the at least one sensor for the measurement of the local tissue blood flow (F) detects a region of up to 2 cm distance from a contact surface of the transcutaneous sensor.

* * * * *